United States Patent [19]
Ruschke

[11] Patent Number: 6,149,672
[45] Date of Patent: Nov. 21, 2000

[54] DEVICE FOR THE AMPLIFICATION OF ELECTROMAGNETIC OSCILLATIONS IN ORDER TO INFLUENCE A BIOLOGICAL SYSTEM

[76] Inventor: Thomas Ruschke, Willy-Brandt-Strasse 3, 24340 Eckernfoerde, Germany

[21] Appl. No.: 09/160,339

[22] Filed: Sep. 25, 1998

[30] Foreign Application Priority Data

Sep. 25, 1997 [DE] Germany .......................... 197 42 262
Sep. 3, 1998 [DE] Germany .......................... 198 40 173

[51] Int. Cl.[7] .................................................. A61N 5/00
[52] U.S. Cl. .............................................. 607/89; 607/93
[58] Field of Search .............................. 607/88, 89, 90, 607/92, 93; 600/26–28; 434/236–238

[56] References Cited

U.S. PATENT DOCUMENTS

| | | | |
|---|---|---|---|
| 5,149,317 | 9/1992 | Robinson | 600/28 |
| 5,151,080 | 9/1992 | Bick | 600/28 |
| 5,409,445 | 4/1995 | Rubins | 600/27 |
| 5,445,146 | 8/1995 | Bellinger . | |
| 5,914,914 | 6/1999 | Moran | 600/28 |

*Primary Examiner*—Linda C. M. Dvorak
*Assistant Examiner*—Bryan K. Yarnell
*Attorney, Agent, or Firm*—Pillsbury Madison & Sutro

[57] ABSTRACT

A system including a device for the coherent amplification of electromagnetic oscillations by induced emission through a solid element, crystals or glasses doped with neodymium, semiconductor diodes or liquids or gases, and a cable or optical fiber cable for conducting the electromagnetic oscillations emerging from the device in order to influence a biological system, especially a human body or an animal body 11. The cable 2 has an outlet opening 7 and the oscillations or beams emerging from the cable 2 are conducted through a solid element, a mixture or a liquid or gaseous solution 8 in order to influence the biological system 11. The solid element, the mixture or the liquid or gaseous solutions contain mineral, plant, animal or human extracts or products or else toxins as admixtures.

20 Claims, 4 Drawing Sheets

DEVICE FOR THE AMPLIFICATION OF ELECTROMAGNETIC OSCILLATIONS IN ORDER TO INFLUENCE A BIOLOGICAL SYSTEM

BACKGROUND OF THE INVENTION

The invention relates to a device for the amplification of electromagnetic oscillations in order to influence a biological system.

Devices are already known which are used in the field of medicine for the coherent amplification of electromagnetic oscillations by means of induced emission through a solid element. With the known lasers, there is an interest in high pulsed power and bundling of the laser beams. Currently, only detachment of the retina and certain types of brain cancer are treated with laser beams. The treatment of detachment of the retina is simple and the patient does not have to be anesthetized. After the surgeries that have been performed so far, patients who have been operated on do not feel any pain, and they only perceive a glare for some time, which is due to the effect of the laser light and to chemical processes on the retina or in the optic nerve. As far as treatment of cancer in the brain with laser beams is concerned, the selected site is struck by the laser beam, causing vaporization of the tissue.

BRIEF SUMMARY OF THE INVENTION

In contrast to this, the invention is based on the objective of improving the device for the coherent amplification of electromagnetic oscillations by means of induced emission as compared to the prior art laser devices and of exerting a positive influence on a biological system and/or of considerably accelerating the curative treatment, for example, the healing of wounds, burns, broken bones, tumors, contusions or bruises.

The objective is achieved according to the invention in that a) the device has a recording and/or playback unit for an analog or digital sound signal and/or a storage device for an analog or a digital sound signal, b) the output of at least one of these units relays the sound signal to a sound signal pick-up or converter that is connected to said output, c) the sound signal pick-up or converter is operationally connected to a device for the coherent amplification of electromagnetic oscillations or to a device for the amplification of electromagnetic oscillations or to a laser device, d) the electromagnetic oscillations emerging from the laser device are conducted through a cable or optical fiber cable in order to influence a biological system, especially a human or animal body.

Due to the advantageous configuration of the device for the amplification of electromagnetic oscillations in order to influence a biological system, it becomes possible to use sound signals that can be retrieved, for example, from a sound storage device or from a CD player, for curative treatment. For this purpose, the oscillations are advantageously transmitted to a certain site on the body, especially at the site of the immune point, thus acting upon the human body. Depending on the type of person, suitable, specially modulated oscillations can be provided. Thus, the sound signals are not detected acoustically as had been the case until now. The sound signals serve to control a device linked to the laser device, so that the operating voltage of the laser fluctuates to differing extents, for example, between 1 mV and 6 mV. As a result, the laser beam is transmitted to the human body in a pulsed manner, depending on the correspondingly modulated sound signal. It has been found that gentle calm music is especially well-suited. Depending on the type of person, an appropriate type of music should be selected.

In contrast to the technical or thermal effect that has been associated with the use of laser technology until now such as, for example, pulverizing, cutting, welding or vaporizing, the System according to the invention and the interaction between the admixtures and the electromagnetic beams in the visible range have brought specific effects to the fore, and as a result, these admixtures can be used in a curative manner.

An effective healing is achieved within a short time in an optimal manner through the interaction between the light beams and the substances contained in the solid elements or mixtures. By means of the laser beam, the biological system receives the necessary energy in conjunction with the substance-specific information while utilizing the Ramann effect. In the case at hand, for example, a wound was first cared for in the classical medical manner and treated with antibiotic bandages. At the beginning of the treatment, the wound had a length of 18 cm and a width of 2.5 cm in the middle. Raw flesh could be seen in the wound. The laser irradiation, in conjunction with the substance incorporated into the laser beam in a concentration of 100 vol.-% to $10 \times 10^{-24}$ vol.-%, was able to effectuate optimal healing within an extremely short period of time, i.e. in three weeks. This is also achieved in an advantageous manner in that, through the emerging light, the laser beam conducted through the substance receives information that optically corresponds to the fingerprint of the incorporated substance. In any case, the emerging laser beam is conducted through the solid element or the liquid or gaseous solution with the admixture that functions as the optical device and said beam is directed at the wound. The treatment of a wound having a surface area of 25 cm$^2$ can take 30 minutes. Such a treatment over the course of a week on a daily basis brings about an intense healing reaction, whereby the wound size finally shrinks to 4 cm$^2$ and has a circular scab after about two weeks. If such a treatment process is continued over a period of three weeks, a wound having a surface area of 25 cm$^2$ can heal completely.

In this context, it is especially advantageous that the device can be used for the amplification of electromagnetic oscillations by means of induced emission through a solid element, crystals or glasses doped with neodymium, semiconductor diodes or liquids or gases, whereby the electromagnetic oscillations emerging from the device are conducted through a cable or optical fiber cable in order to influence a biological system, especially a human or animal body, whereby the cable has an outlet opening and the oscillations or beams emerging from the cable are conducted through a solid element, a mixture or a liquid or gaseous solution in order to influence the biological system, whereby the solid element, the mixture or the liquid or gaseous solutions contain mineral, plant, animal or human extracts or products or else toxins as admixtures.

It is also advantageous for the cable to have an inlet opening as well as an outlet opening, whereby the outlet opening opens up into the inlet opening of a treatment probe and the solid element, the mixture or the gaseous or liquid solution is provided or can be placed between the inlet and outlet openings.

The curative treatment can be considerably improved by using certain media that can be incorporated into the laser beam.

In another embodiment of the invention, it is advantageous for the converter to be installed between a sound playback unit or a CD playback unit and the laser device.

It is also advantageous for the laser device to be associated with a control device that is installed between the converter and the laser device and/or is operationally connected to them.

In another embodiment of the invention, it is advantageous for the converter to have at least one input for a modulated signal or sound signal that is conducted through at least one voltage regulator and at least one feedback to an output which is connected to the input of the control device and/or to the input of the laser device.

According to another feature of the System according to the invention, it is advantageous for the control device to have an amplifier and for the output of the control device to be connected to the laser device.

Moreover, it is advantageous for the laser to be designed as an argon-ion-krypton mixed-gas laser.

Another possibility according to an embodiment of the System according to the invention is for the laser to be designed as an He-Ne laser.

In another embodiment of the invention, it is advantageous for the laser to be designed as an He-Cd laser.

Moreover, it is advantageous for the laser to be designed as a multi-line/single-line, multi-mode or variable-frequency laser.

In another embodiment of the invention, it is advantageous for the laser to be designed as a diode laser for frequencies from $5 \times 10^{14}$ Hz to $10^{15}$ Hz.

An additional possibility according to another embodiment of the device of the invention is for the laser to be designed as a crystal laser or as a neodymium-yag laser.

It is also advantageous that a solid element or a gaseous or liquid mixture that is present in a concentration of $10 \times 10^{-3}$ vol.-% to $10 \times 10^{-9}$ vol.-% can placed into the receptacle for the treatment of contusions.

An essential advantageous embodiment is achieved in that a solid element or a gaseous or liquid mixture that is present in a concentration of $10 \times 10^{-3}$ vol.-% to $10 \times 10^{-12}$ vol.-% can be placed into the receptacle for the treatment of broken bones, whereby the argon-ion laser device is used for this purpose.

Moreover, it is advantageous that a solid element or a gaseous or liquid mixture that is present in a concentration of $10 \times 10^{-6}$ vol.-% to $10 \times 10^{-8}$ vol.-% can be placed into the receptacle for the treatment of tumors, whereby the argon-krypton mixed-gas laser device is used for this purpose.

Furthermore, it is advantageous that a solid element or a gaseous or liquid mixture that is present in a concentration of $10 \times 10^{-3}$ vol.-% to $10 \times 10^{-9}$ vol.-% can be placed into the receptacle for the treatment of concussions, whereby the argon-ion laser device is used for this purpose.

An additional possibility is that a solid element or a gaseous or liquid mixture that is present in a concentration of $10 \times 10^{-1}$ vol.-% to $10 \times 10^{-24}$ vol.-% can be placed into the receptacle for the treatment of metabolic disorders, whereby the argon-ion and/or argon-krypton mixed-gas and/or diode and/or neodymium-yag and/or He-Ne and/or He-Cd laser device is used for this purpose.

An arrangement for carrying out the process according to the invention is that a solid element or a gaseous or liquid mixture that is present in a concentration of 100 vol.-% to $10 \times 10^{-24}$ vol.-% can be placed into the receptacle for the treatment of cell cultures, whereby the argon-ion, argon-krypton, krypton, diode, neodymium-yag, He-Ne, or He-Cd laser device is used for this purpose.

The concentrations given in this description are homogeneous mixtures of various substances. For practical purposes, the concentration of a given substance is preferably expressed in percent by weight or by volume (weight or volume proportion×100 vol.-%). For theoretical considerations, the mol fraction (mols per sum of the mols), the molarity (mols per liter of solution) or the molality (mols per kg of solvent) constitute a suitable measure of concentration.

Further advantages and details of the invention will explained below with reference to the drawing.

DETAILED DESCRIPTION OF THE INVENTION

Figure 1:
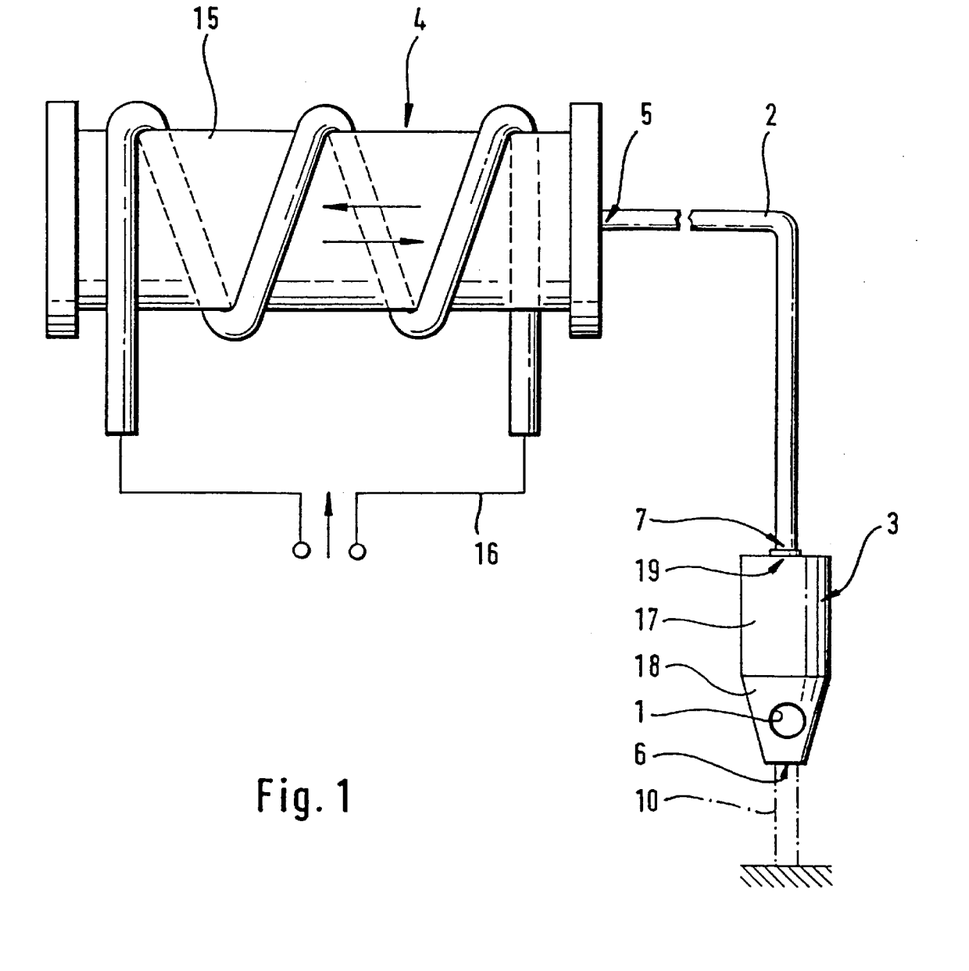
FIG. 1 is an elevational view of a laser System according to the invention with a cable or optical fiber cable provided at the outlet opening of the laser device.

In FIG. 1 of the drawing, a device for the coherent amplification of electromagnetic oscillations is designated with the numeral 4. The device 4 consists of a laser tube 15 containing an argon-ion gas, for example, for burns. Energy is transmitted to the laser device 4 through an electric line 16. The electromagnetic oscillations, waves or the laser beam emerging from the laser device 4 can have frequencies of $5 \times 10^{14}$ Hz to $10^{15}$ Hz (visible range). Depending on the curative treatment or type of application, the laser device can be designed in such a way that it can be used in the ultraviolet or infrared range. The frequencies given here constitute the visible part (light) of the electromagnetic spectrum.

A laser beam or a light beam 10 is conducted through a cable 2 whose inlet opening 5 is connected to the laser device 4 and to its outlet opening, and to an inlet opening 19 of a treatment probe or receptacle 3. The laser beam 10 emerges to the outside via the outlet opening 6 and is directed at a biological system 11.

Figure 2:
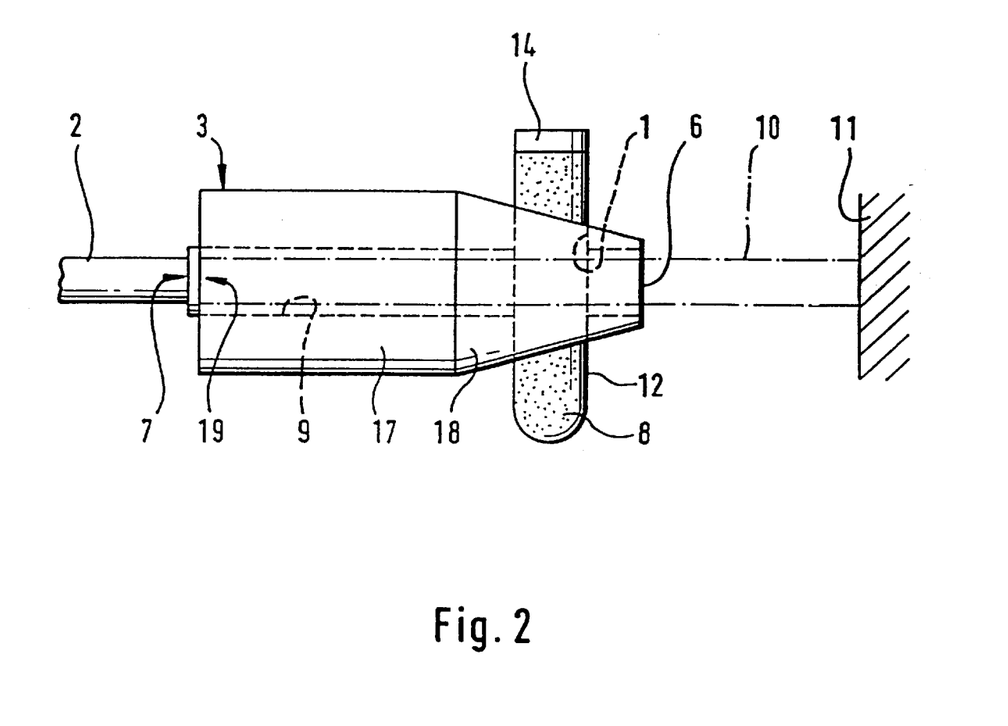
FIG. 2 is an elevational view of a treatment probe or a receptacle constituting a component of the device of FIG. 1.

The receptacle 3 consists of a cylindrical housing part 17 with an adjacent housing part 18 that is tapered towards the front. Over the entire length of the receptacle 3, there is a longitudinal opening 9 that opens up into the outlet opening 6. Thus, the light or laser beam 10 is conducted via the longitudinal opening 9, said light or laser beam is then conducted via the outlet opening 6 provided in the receptacle, it strikes the biological system 11 or a human body, an animal body or a plant body, where it brings about the desired healing effect or change in the biological system. In the range of the outlet opening 6 of the receptacle 3, there is a crosswise opening 1 that intersects the longitudinal opening 9 at an angle, advantageously at a right angle.

As can be seen in FIG. 2, a container 12 is inserted into the crosswise opening 1 in such a way that it intersects the beams of the laser beam at an angle of 90°. As a result, the laser beams are conducted via or through the container 12.

The container 12 is advantageously made of glass, especially of quartz glass, so that almost no losses occur when the laser beam passes through the quartz glass.

Therefore, the container 12 can advantageously be cylindrical in shape. However, it is also possible to configure the container 12 so as to be conical and to adapt the corresponding crosswise opening 1 likewise to the conical shape of the container 12 so that a clamp connection between the receptacle 3 and the container 12 is achieved.

The container 12 serves to receive one or more solid elements or else to receive substances in pulverulent form or to receive a gaseous or liquid solution. In addition, a carrier solution, for example, water and ethanol at a ratio of 1:1, can be filled into the container 12. The admixtures or substances are placed into the carrier solution in a concentration of 50 vol.-% to $10 \times 10^{-24}$ vol.-% in a decreasing direction. Additionally, for example, mineral, plant, animal or human extracts or products or else toxins are added to this carrier solution. These additives are referred to as admixture 8, which is decisive for exerting a positive influence on the biological system 11 or for the medical treatment in question.

Thus, the filling of the container 12 can be a true solution, a solution mixture or a colloidal solution. Depending on the composition of the admixture, it is also possible to do without the carrier solution.

The laser beam 10 is conducted through the container 12 with the substances or admixtures and then strikes the biological system 11. In an advantageous manner, the light radiation is specifically scattered (utilization of the Ramann effect) in every atomic or molecular compound, and the emerging light practically contains the fingerprint of the admixtures. If, for example, an argon-ion laser is used, this laser beam provides the appropriate basic energy for the biological processes. The emerging laser beam then passes on the information to the biological system and brings about the healing process, for example, in the case of a burn.

The distance between the outlet end of the receptacle 3 and the biological system 11 is usually constant during the treatment process. If the distance between the outlet end of the receptacle 3 and the biological system 11 is increased, then a larger surface area of the biological system is also reached by the laser beam 10.

If a neodymium-yag laser is used, for instance, for treating wounds or for another type of treatment, it is advantageous if the wavelength of 532 nm (green) and 473 nm (blue) are used.

It is especially advantageous for the laser emission to lie in the visible range, that is to say, between 650 nm and 300 nm (UV). The selection of the wavelength depends on which biological system 11 is to be irradiated. Infrared light should not be used for human cells since it can kill them.

If the laser device is used, for example, for tumor treatment, then the laser consists of an argon-ion-krypton mixed-gas laser between 2 mm and 100 mm.

In this case, the following admixtures are placed into the container:
a) Local: extracts from pathogens of tuberculosis and/or gonorrhea and/or syphilis in a concentration of $10 \times 10^{-6}$ vol.-% to $10 \times 10^{-8}$ vol.-%.
b) Limbic system (brain): extract from Salamandra $10 \times 10^{-6}$ vol.-% to $10 \times 10^{-8}$ vol.-%.

For the treatment of broken bones, it is advantageous to use an argon-ion laser device between 2 mm and 100 mm. For this treatment, substances of the type listed below are used as admixtures.

The explanations given above show that a very specific type of laser with a corresponding probe has to be used for the medical treatment of the biological system 11, depending on the type of illness, whereby a certain admixture 8 is incorporated into each probe or receptacle.

A patient born in 1927 was found to have an open wound on the left thigh that would not heal. This wound could not be positively influenced by any of the classical treatments (e.g. administration of antibiotics, surgical treatment of the edge of the wound). This wound was treated with the described argon-ion laser, whereby the frequencies emitted were in the visible range. The power output of the laser device 4 was 50 mW. The laser beam 10 was directed at the burn 11 through the substances 8 present in the quartz glass container 12. Several substances were contained in the carrier solution in the following concentration: extract from Aconitum $10 \times 10^{-4}$ vol.-% and extract from Arnica $10 \times 10^{-3}$ vol.-%.

The emerging laser beam 10, as already mentioned, was radiated over the entire wound through the container 12 that functioned as an optical device. The treatment duration was 30 minutes each time. Already after a week, an intense healing reaction set in. After one week of treatment, the wound that had been 10 cm long and 2.5 cm wide in the middle at the beginning of the laser treatment was 2 cm in diameter after one week and 7 mm in diameter after two weeks. After three weeks, the wound had healed completely.

The laser radiation was used successfully for treating wounds, broken bones, sprains, compressions and concussions.

Following a severe concussion and laser treatment applied within five minutes, the patient was already completely free of symptoms after a ten-minute treatment, and a normal neurological reaction was observed.

Depending on the type of treatment, the appropriate laser with the appertaining container 12 containing an appropriate admixture is used.

The laser treatment or irradiation can also exert a positive influence on the metabolism. The appropriate admixtures contain extracts from plants, from animal and human products, also extracts from viruses, bacteria, fungi and other pathogens as well as extracts from tumors and pathological secretions.

Cell cultures and living cells can be positively influenced in the case of organ donation. Moreover, it is advantageous to use the laser radiation for microorganisms and also viruses outside of living organisms.

The following solutions have been successfully used for wound treatment in the following concentrations:

| | |
|---|---|
| Extract from Aconitum | $10 \times 10^{-4}$ vol.-% |
| Extract from Arnica | $10 \times 10^{-3}$ vol.-% |
| Extract from Belladonna | $10 \times 10^{-4}$ vol.-% |
| Extract from Bellis | $10 \times 10^{-4}$ vol.-% |
| Extract from Calendula | $10 \times 10^{-5}$ vol.-% |
| Extract from Chamomilla | $10 \times 10^{-4}$ vol.-% |
| Extract from Echinacea ang. | $10 \times 10^{-4}$ vol.-% |
| Extract from Echinacea purp. | $10 \times 10^{-4}$ vol.-% |
| Extract from Hamamelis | $10 \times 10^{-3}$ vol.-% |
| Extract from Millefolium | $10 \times 10^{-4}$ vol.-% |
| Extract from Symphytum | $10 \times 10^{-9}$ vol.-% |
| Solution of Hepar sulf. | $10 \times 10^{-9}$ vol.-% |
| Solution of Mercurius sol. | $10 \times 10^{-9}$ vol.-% |
| Solution of Quartz | $10 \times 10^{-6}$ vol.-% |

These and other concentrations are placed into the container 12. The container 12 functions as an optical element or as a lens and amplifies the laser beam 10. When the laser beam strikes an atom or molecule, the laser beam is scattered, i.e. the above-mentioned Ramann effect is utilized. The emerging laser beam contains the above-mentioned optical fingerprint of the substances listed above and has an influence on the treatment of the biological system 11. The scattered beams produce a bio-photon field.

Argon-ion lasers are used to treat broken bones, and substances 8 are placed into the container 12. This admixture or substance has a concentration of $10 \times 10^{-3}$ vol.-% to $10 \times 10^{-12}$ vol.-%.

A red diode laser 632 nm is used for the treatment of wild roses and a mixed quartz is added in the concentration of $10 \times 10^{-6}$. (When wild roses are treated with a laser, germs or fungi can be controlled, and wild roses can be grafted better after a laser treatment. This underscores the fact that a laser treatment can easily be carried out in plants.)

If, for example, the laser device is used for allergy treatment, then the laser consists of a red He-Ne or diode laser at 632 nm and a green He-Ne/neodymium-yag laser.

In this case, the following admixtures are placed into the container: extract from Dioscorea vilosa in the concentration of $10 \times 10^{-5}$ vol.-% and Kalium carb. in the concentration of $10 \times 10^{-6}$ vol.-%.

For treating hair loss, the laser consists of a green He-Ne or neodymium-yag laser.

In this case, the following admixtures are placed into the container: extract from tuberculosis and/or placenta and/or extract from Pel talpae in the concentration of $10 \times 10^{-3}$ vol.-% to $10 \times 10^{-9}$ vol.-%.

If the laser device is used for treating enteritis, then the laser consists of a green He-Ne or neodymium-yag laser alternating with a yellow He-Ne laser.

In this case, the following admixtures are placed into the container: extracts from pathogens in the concentration of $10 \times 10^{-4}$ to $10 \times 10^{-12}$ vol.-%.

If the laser is used, for example, for the treatment of circulatory disorders, then the laser consists of a red He-Ne diode laser.

In this case, the following admixtures are placed into the container: extracts from pathogens and/or snake venom in the concentration of $10 \times 10^{-4}$ vol.-% to $10 \times 10^{-12}$ vol.-%.

In order to treat eczema, the laser consists of a green laser alternating with an argonion multi-line laser.

In this case, the following admixtures are placed into the container: extracts from pathogens in the concentration of $10 \times 10^{-4}$ to $10 \times 10^{-12}$ vol.%

For the treatment of lowered resistance (weakened immune system), the laser consists of a red He-Ne diode laser.

In this case, the following admixtures are placed into the container: extracts from pathogens in the concentration of $10 \times 10^{-4}$ to $10 \times 10^{-12}$ vol.-%.

In order to treat hepatic colic, the laser consists of a green He-Ne or neodymium-yag laser.

In this case, the following admixtures are placed into the container: extracts from pathogens, magnesium phosphate and calcium phosphate in the concentration of $10 \times 10^{-4}$ vol.-% to $10 \times 10^{-12}$ vol.-%.

If the laser is used, for example, for the treatment of stomach ailments, then the laser consists of a red He-Ne diode laser.

In this case, the following admixtures are placed into the container: extracts from pathogens in the concentration of $10 \times 10^{-4}$ to $10 \times 10^{-12}$ vol.-%.

If the laser device is used to treat joint disorders, then the laser consists of an argon-ion multi-line laser.

In this case, the following admixtures are placed into the container: extracts from pathogens in the concentration of $10 \times 10^{-4}$ to $10 \times 10^{-12}$ vol.-%.

For the treatment of digestive organs and the kidneys, the laser consists of a yellow and a green He-Ne laser.

In this case, the following admixtures are placed into the container: extracts from pathogens in the concentration of $10 \times 10^{-4}$ to $10 \times 10^{-12}$ vol.-% and/or minerals in the concentration of $10 \times 10^{-3}$ vol.-% to $10 \times 10^{-24}$ vol.-% and/or extract from Salamandra in the concentration of $10 \times 10^{-8}$ vol.-%.

If the laser is used for the treatment of Herpes and Herpes zoster, then the laser consists of an argon-ion multi-line laser.

In this case, the following admixtures are placed into the container: extract from tuberculosis in the concentration of $10 \times 10^{-6}$ vol.-%.

For the treatment of neuritis (ischialgia), the laser consists of an argon-ion multi-line laser.

In this case, the following admixtures are placed into the container: extract from tuberculosis in the concentration of $10 \times 10^{-6}$ vol.-%.

In order to treat cardiac insufficiency, anginal disorders, the laser consists of an orange He-Ne laser.

In this case, the following admixtures are placed into the container: extracts from pathogens in the concentration of $10 \times 10^{-4}$ to $10 \times 10^{-12}$ vol.-% and/or minerals in the concentration of $10 \times 10^{-3}$ to $10 \times 10^{-24}$ vol.-% and/or extract from Salamandra in the concentration of $10 \times 10^{-8}$ vol.-%.

If the laser device is used, for example, to treat migraine, then the laser consists of an argon-ion multi-line laser and a red He-Ne diode laser.

In this case, the following admixtures are placed into the container: extract from tuberculosis in the concentration of $10 \times 10^{-6}$ vol.-%.

In order to treat neurodermatitis, the laser consists of an argon-krypton mixed gas laser and a red He-Ne diode laser.

In this case, the following admixtures are placed into the container: extracts from pathogens in the concentration of $10 \times 10^{-4}$ to $10 \times 10^{-12}$ vol.-% and/or minerals in the concentration of $10 \times 10^{-3}$ to $10 \times 10^{-24}$ vol.-% and/or extract from Salamandra in the concentration of $10 \times 10^{-8}$ vol.-% and an extract from Dioscorea vilosa in the concentration of $10 \times 10^{-5}$ vol.-% and Kalium carb. in the concentration of $10 \times 10^{-6}$ Vol.-%.

If the laser is used to treat Parkinson's disease, then the laser consists of argon-ion multi-line laser and an argon-krypton mixed-gas laser.

In this case, the following admixtures are placed into the container: extracts from pathogens in the concentration of $10 \times 10^{-4}$ to $10 \times 10^{-12}$ vol.-% and extracts from hormones in the concentration of $10 \times 10^{-6}$ to $10 \times 10^{-24}$ vol.-%.

Figure 3:
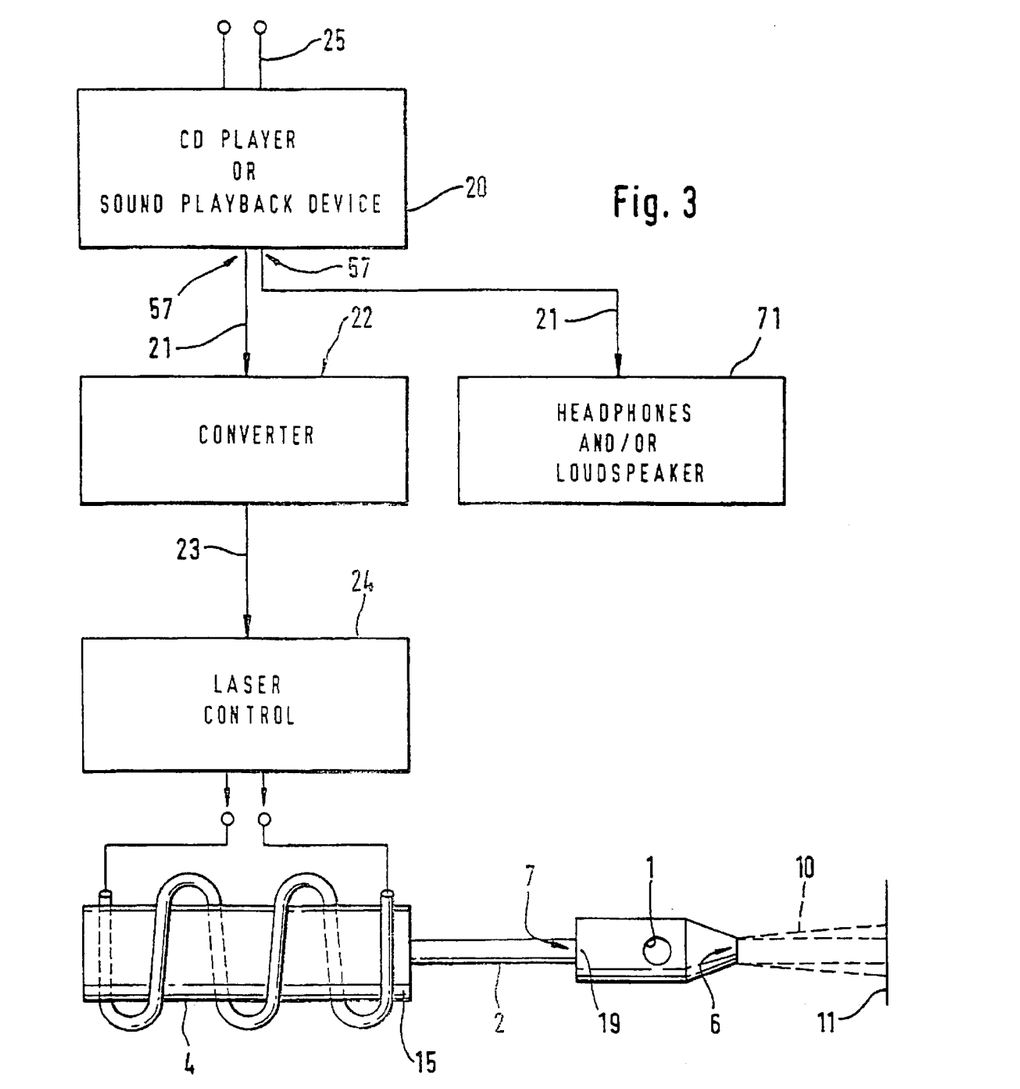
FIG. 3 is partly an elevational view and partly a block diagram showing another embodiment of a laser device with a sound playback unit or storage device installed upstream from the laser device.

FIG. 3 shows another embodiment of device 4 for the amplification of electromagnetic oscillations in order to influence a biological system 11. This device has a recording or playback unit for an analog or digital sound signal and/or a sound playback device 20 with an input line 25 that can be connected to a source of power. A storage device that can store modulated signals, especially sound signals, is described below. It is installed upstream from the laser device and thus influences the power supply as a function of the intensity of the sound signal.

As can be seen in FIG. 3, the CD player or sound playback device 20 is connected via a line 21 directly or indirectly with an input of a converter 22. The converter 22 is shown in detail in FIG. 4.

The output of the converter 22 is connected via a line 23 to a control device 24 for the laser. The outputs of the control device 24 are connected to the inputs of the power supply of the laser device 4.

If, for example, the sound signal is fed from the CD player via the line 21 to the control device for the laser, then, as a function of the sound signals that are converted into current signals by means of the converter, the laser is supplied with differing voltage so that the intensity of the laser beam 4 changes continuously as a function of the sound signal from the CD player 20. This so-called modulated or influenceable laser beam 4 is then conducted through the treatment probe 3 to the biological system or the human body 11. For this purpose, it is advantageous for the laser beam 4 to penetrate at the immune point into the human body. As described above, the substances placed into the container 12 are varied, depending on the illness.

The laser device 4 can be designed, for example, as a diode laser and can have three inputs for this purpose. One of the inputs serves for the supply voltage that can advantageously lie between 3 and 10 volts, but especially between 4 and 5 volts. Furthermore, the laser has an input for a positive modulation signal and another input for a negative modulation signal.

The modulation input is operated by very low control currents (<500 mA). As already mentioned, it is designed for voltages between 2 and 10 volts, especially between 6 and 8 volts.

The signal that is coming from the CD player and then converted is transmitted to the input (supply voltage) of the laser device 4 via a transducer 22. Through the different frequencies, the currents that emerge from the converter also vary in strength and lie between 6 and 8 volts. The modulated current signal influences the intensity of the emitted laser beam at the opening 6 of the device 4. In this manner, laser beams of different strengths strike the human body 11, thus influencing the healing process. Although it is possible for the laser beam that emerges from the laser device 4 to be conducted directly onto the human body 11, it is especially advantageous for the laser beam to be conducted through a substance 8 contained in the container 12. This considerably improves the healing effect. The substances 8 present in the container 12, as already mentioned, depend on the type of treatment.

Figure 4:
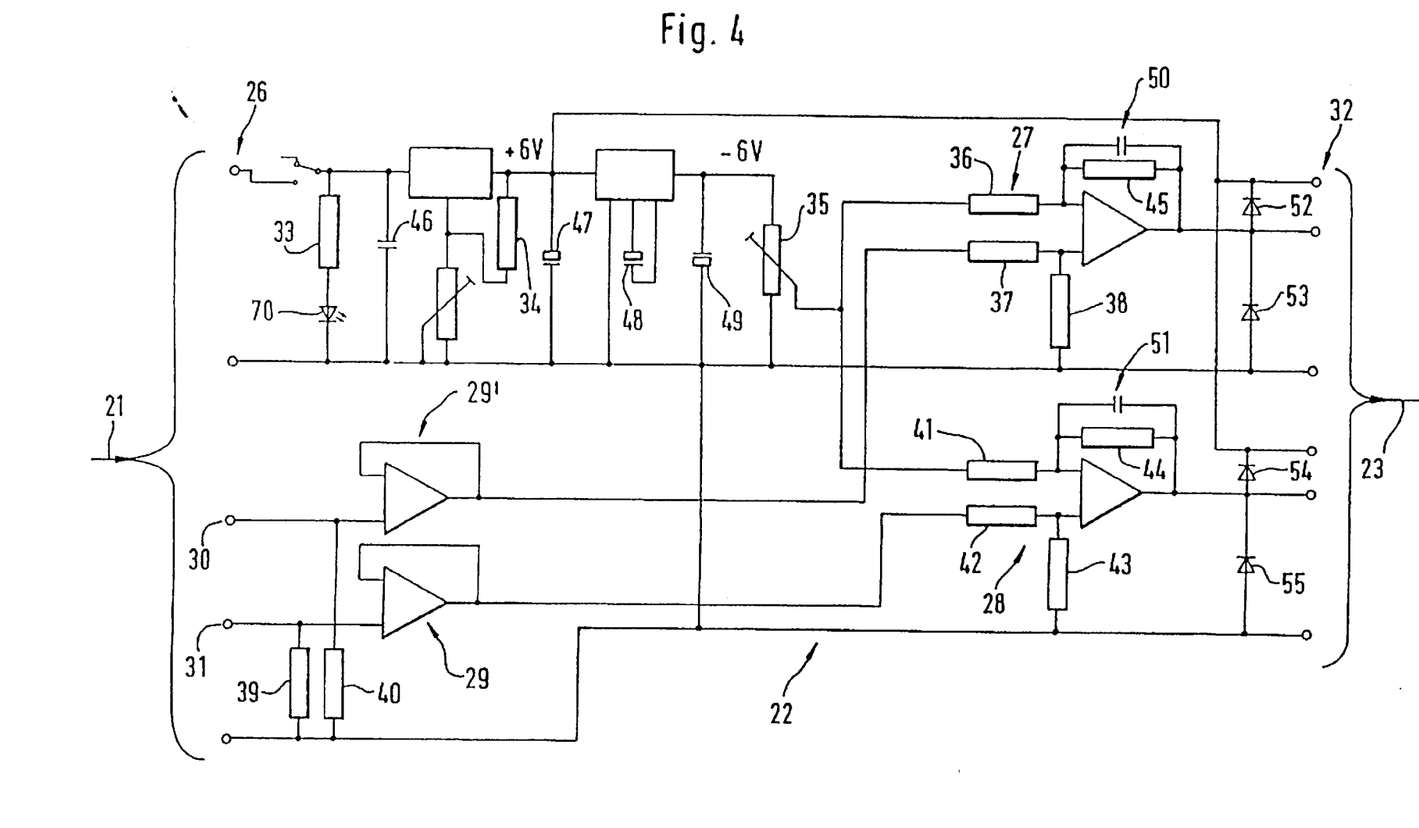
FIG. 4 is a circuit diagram of a converter constituting one component of the embodiment of FIG. 3 that is installed upstream from the laser device.

FIG. 4 shows the converter or the information value transmitter 22. The converter 22 serves to convert the electrical quantities that come from the sound playback unit. Possibilities are attenuation, elongation, sound oscillation, magnetic or optical radiation quantities. They are all converted into corresponding electrical quantities and can thus be transmitted precisely to the control device 24 or directly to the laser without disrupting the process. These different current pulses or surges, which are influenced by the sound signal, are transmitted to the control device of the laser and, as already described, influence the laser beam. For this purpose, the converter has two inputs 30 and 31 (Channel I and Channel II) which are each connected to the output 23 via a voltage regulator 29, 29' and via a feedback device 51. The converter 22 can be connected to a source of voltage via a switch 26. The current supply side of the converter 22 has resistors 33, 34, 35, 36, 37, 38, 45 that are connected to the supply lines via appropriate lines. Moreover, the converter has the condensers 46, 47, 48, 49 and 50 as well as the diodes 52, 53 and 70. Behind the inputs 30 and 31, Channels 1 and 2 contain the resistors 39, 40, 41, 42, 43 and 44 as well as the diodes 54 and 55.

Details on the resistors, diodes and condensers of the voltage controller and on the feedback as well as the on function can be seen in FIG. 4.

It is especially advantageous to use classical music or other gentle music. Due to its one-sided nature, any other music, for example, techno-music or pulsed lasers, technically regulated or randomly generated, e.g. 1000 Hertz, which constitutes an acoustic signal in the broadest sense of the word, can have a harmful effect on the internal balance of biological systems.

The use of music, especially harmonic, soothing selections, protects the system from one-sided effects.

A monotonous, constant humming tone, like the sound heard at a construction site, can be painful in the long run.

Treatment with music, using harmonic sound sequences, brings about an intensification of the effect and avoids exerting a one-sided, monotonous influence on the biological system.

Reverting to FIG. 3, the device or the recording unit for an analog or digital sound signal, sound playback unit, storage device, CD player 20 through which sound information or music information is produced, rendered useable and/or transmitted to another means has one or more outputs 57, 57'. One output 57 is connected indirectly to the laser device 4 and the other output 57' is connected directly or indirectly to headphones and/or to at least one loud-speaker 71. In this manner, the patient to be treated is influenced in two ways with modulated oscillations or by music, which has a very positive influence on the course of the illness of the patient.

In the embodiment, the CD player or the sound playback device 20 can be replaced by any other device with which the modulated tones, for example music, can be produced and transmitted to another device.

In the embodiment according to FIG. 3, at the output of such a device, for example, on the CD player 20, the output 57' is parallel to the output 57 and is connected either directly or indirectly to loudspeakers or to headphones. The output 57' can be connected to the headphones or to the loudspeakers either via an electric line or else by radio means. This is to ensure that the music pulses that are normally conveyed to the device 4 or to the laser can also be transmitted in parallel to headphones or to loudspeakers. In this manner, the person to be treated is influenced or treated indirectly by the inaudible pulse signals from the laser 4 and, in parallel, is additionally treated with acoustic signals that have been rendered audible. It has been found that the treatment outcome can be considerably improved if the sound pulses are applied to the person to be treated in two different ways.

This application relates to subject matter disclosed in German Application number 197 42 262.4, filed on Sep. 25, 1997, the disclosure of which is incorporated herein by reference.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

List of reference numerals

1 crosswise opening
2 cable, optical fiber cable
3 treatment probe, receptacle, probe
4 device for the coherent amplification of electromagnetic oscillations (laser device)=laser
5 inlet opening of cable 2
6 outlet opening of device 4

7 outlet opening of cable 2
8 admixture; solid element, mixture, liquid or gaseous (substance) solution
9 longitudinal opening
10 electromagnetic oscillations, waves, laser beam or beam path of the laser beam
11 biological system, human body, animal body (burn injury)
12 container
14 closure mechanism
15 laser tube
16 electrical line
17 housing part of the receptacle 3
18 housing part of the receptacle 3
19 inlet opening of the receptacle 3
20 recording device for an analog or digital sound signal, sound playback unit, storage device, CD player
21 line
22 sound signal pick-up, converter
23 line of the converter 22, output
24 control device
25 input line
26 switch
27 feedback
28 feedback
29 voltage regulator
29' voltage regulator
30 input, channel I
31 input, channel II
33 resistor
34 resistor
35 resistor
34 resistor
36 resistor
37 resistor
38 resistor
39 resistor
40 resistor
41 resistor
42 resistor
43 resistor
44 resistor
45 resistor
46 resistor
47 condenser
48 condenser
49 condenser
50 condenser
51 feedback
52 diode
53 diode
54 diode
55 diode
57 output of CD player
70 diode

What is claimed is:

1. System for the amplification of electromagnetic oscillations in order to influence a biological system, comprising:
   a) a first unit which is at least one of a recording unit, a playback unit, a recording and playback unit, and a storage device (25) for an analog or a digital sound signal, said first unit having an output;
   b) a second unit which is one of a sound signal pick-up and converter (22) that is connected to said output;
   c) a third unit which is one of a device for the coherent amplification of electromagnetic oscillations, a device for the amplification of electromagnetic oscillations and a laser device (4), operationally connected to said second unit; and
   d) a cable or optical fiber cable (2) connected for conducting the electromagnetic oscillations emerging from said third unit in order to influence a biological system, a human or animal body (11).

2. System according to claim 1, wherein said third unit amplifies electromagnetic oscillations by means of induced emission through a solid element, crystals or glasses doped with neodymium, semiconductor diodes or liquids or gases, whereby the electromagnetic oscillations emerging from the device are conducted through the cable in order to influence the biological system, human or animal body (11), whereby the cable (2) has an outlet opening (7) and the oscillations or beams emerging from the cable (2) are conducted through a quantity of a substance composed of a solid element, a mixture or a liquid or gaseous solution (8) in order to influence the biological system (11), wherein the solid element, the mixture or the liquid or gaseous solutions contain mineral, plant, animal or human extracts or products or else toxins as admixtures.

3. System according to claim 2, wherein the cable (2) has an inlet opening (5) and the outlet opening (7), wherein the outlet opening (7) opens up into the inlet opening (19) of a treatment probe and the substance (8) is provided or can be placed between the inlet and outlet openings (19, 6).

4. System according to claim 2, wherein the substance (8) is present in a concentration of $10 \times 10^{-3}$ vol.-% $10 \times 10^{-9}$ vol.-% and is placed into a receptacle (3) for the treatment of contusions.

5. System according to claim 2, wherein the substance (8) is present in a concentration of $10 \times 10^{-3}$ vol.-% to $10 \times 10^{-12}$ vol.-% and is placed into a receptacle (3) for the treatment of broken bones, and the third unit is an argon-ion laser.

6. System according to claim 2, wherein the substance (8) is present in a concentration of $10 \times 10^{-6}$ vol.-% to $10 \times 10^{-8}$ vol.-% and is placed into a receptacle (3) for the treatment of tumors, and the third unit is an argon-krypton mixed-gas laser.

7. System according to claim 2, wherein the substance (8) is present in a concentration of $10 \times 10^{-3}$ vol.-% to $10 \times 10^{-9}$ vol.-% and is placed into a receptacle (3) for the treatment of concussions, and the third unit is an argon-ion laser.

8. System according to claim 2, wherein the substance (8) is present in a concentration of $10 \times 10^{-1}$ vol.-% to $10 \times 10^{-24}$ vol.-% and is placed into a receptacle (3) for the treatment of metabolic disorders, and the third unit is an argon-ion laser, or an argon-krypton mixed-gas laser, or a diode laser, or an Nd-YAG laser, or an He-Ne laser, or an He-Cd laser.

9. System according to claim 2, wherein the substance (8) is present in a concentration of 100 vol.-% to $10 \times 10^{-24}$ vol.-% and is placed into a receptacle (3) for the treatment of cell cultures, and the third unit is an argon-ion laser, or an argon-krypton laser, or a krypton laser, or a diode laser, or an Nd-YAG laser, or an He-Ne laser, or an He-Cd laser.

10. System according to claim 1, wherein said first unit is one of a sound playback unit and a CD playback unit (20), and the second unit is a converter (22) installed between first unit and the third unit.

11. System according to claim 1, further comprising a control device (24) associated with the third unit.

12. System according to claim 11, wherein the control device (24) is installed between, and operationally connected to, the second unit and the third unit.

13. System according to claim 11, wherein the second unit is a converter (22) having at least one input for a modulated signal or sound signal and further comprising at least one voltage regulator (29) and at least one feedback element (27, 28) having an output (23) that is connected to an input of at least one of the control device (24) and the laser device (4), and the modulated signal or sound signal is conducted through the at least one voltage regulator (29) and at least one feedback element (27, 28) to the output (23).

14. System according to claim 11, wherein the control device (24) has an amplifier.

15. System according to claim 11, wherein the control device (24) has an output connected to the third unit.

16. System according to claim 15, wherein the third unit is an argon-ion-krypton mixed-gas laser.

17. System according to claim 1, wherein the second unit is a converter (22) having at least one input for a modulated signal or sound signal.

18. System according to claim 1, wherein the third unit is an He-Ne laser, or an He-Cd laser, or a multi-line/single-line laser, or a multi-mode or variable-frequency laser, or a diode laser emitting at a frequency between $5\times10^{14}$ Hz and $10^{15}$ Hz.

19. System according to claim 18, wherein the third unit is a crystal laser or a Nd-YAG laser.

20. System according to claim 1, the first unit performs at least one operation from among producing, rendering useable and transmitting sound information or music information and has at least a first output (57) connected to the third unit and at least a second output (57') connected to one of headphones and a loud-speaker (71) directly or indirectly.

* * * * *